(12) United States Patent
Hosaka et al.

(10) Patent No.: US 7,371,870 B2
(45) Date of Patent: May 13, 2008

(54) BENZIMIDAZOLONE COMPOUND

(75) Inventors: Masaki Hosaka, Sakura (JP); Toshio Takei, Kashima (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 557 days.

(21) Appl. No.: 10/534,126

(22) PCT Filed: Jun. 23, 2004

(86) PCT No.: PCT/JP2004/009224

§ 371 (c)(1),
(2), (4) Date: May 6, 2005

(87) PCT Pub. No.: WO2005/000973

PCT Pub. Date: Jan. 6, 2005

(65) Prior Publication Data
US 2006/0058531 A1    Mar. 16, 2006

(30) Foreign Application Priority Data

Jun. 26, 2003  (JP) ............................. 2003-182574
Sep. 22, 2003  (JP) ............................. 2003-329835
Dec. 25, 2003  (JP) ............................. 2003-429203

(51) Int. Cl.
C07D 235/04  (2006.01)
C07D 403/12  (2006.01)

(52) U.S. Cl. ............................. 548/305.4; 548/301.7; 548/302.7; 548/304.4; 548/304.7

(58) Field of Classification Search ............ 548/300.1, 548/301.7, 302.7, 304.4, 304.7, 305.4
See application file for complete search history.

(56) References Cited
U.S. PATENT DOCUMENTS 6,482,817 B1 * 11/2002 Kaul et al. ................. 514/185

FOREIGN PATENT DOCUMENTS

EP    1201718      5/2002
JP    62-101655    5/1987
JP    2001-172520  6/2001

OTHER PUBLICATIONS

W. Herbst, et al.; *Industrial Organic Pigments Second, Completely Revised Edition*; VCH Verlagsgesellschaft mbH, 1997; pp. 345-370 and cover sheet (15 Sheets.)/Discussed in the specification.

* cited by examiner

*Primary Examiner*—Golam M. M. Shameem
(74) *Attorney, Agent, or Firm*—Edwards Angell Palmer & Dodge LLP

(57) ABSTRACT

There are provided benzimidazolone compounds that provide a plurality of hues from a single structural formula, and are useful as pigments that offer superior dispersibility in binder resins, as well as benzimidazolone compounds that are useful as pigments, and show minimal flocculation when pigments of two or more different hues are blended together to produced a desired hue.

A benzimidazolone compound represented by a general formula (1) shown below.

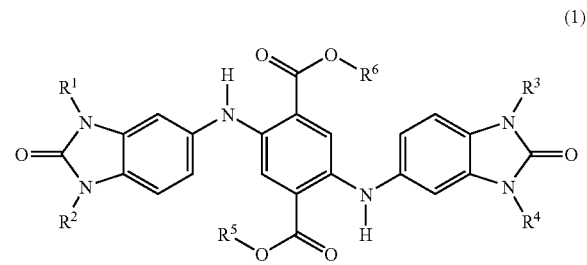

(1)

(wherein, $R^1$, $R^2$, $R^3$ and $R^4$ each represent, independently, a hydrogen atom, an alkyl group of 1 to 5 carbon atoms, or an alkoxy group of 1 to 5 carbon atoms, and $R^5$ and $R^6$ each represent, independently, an alkyl group of 1 to 5 carbon atoms).

6 Claims, 2 Drawing Sheets

BENZIMIDAZOLONE COMPOUND

TECHNICAL FIELD

The present invention relates to benzimidazolone compounds that provide a plurality of hues from a single structural formula, and are useful as pigments that offer superior dispersibility in binder resins.

Priority is claimed on Japanese Patent Application No. 2003-182574, filed Jun. 26, 2003, the content of which is incorporated herein by reference.

BACKGROUND ART

In conventional paints containing dispersed pigments, depending on the nature of the pigment, poor dispersion stability can lead to pigment flocculation, or separation between the pigment and the binder resin (hereafter referred to as "Varnish separation"). One known method for resolving these problems involves the addition of a pigment dispersing agent to the paint. However, although pigment dispersing agents improve the dispersibility of the pigment, they tend to lower the weather resistance and heat resistance of the paint film, and if the pigment dispersing agent is colored, then achieving the desired paint hue can also be difficult.

Furthermore, in the case of a paint with an intermediate color, such as a paint with an intermediate color between red and yellow, pigments of different structural formulas, such as a red colored diketopyrrolopyrrole based pigment, quinacridone based pigment, or diaminoanthraquinone based pigment, and a yellow colored azo based pigment, isoindoline based pigment, or isoindolinone based pigment must be blended together.

Paints containing a plurality of pigments with different structural formulas tend to be more prone to pigment flocculation and varnish separation than paints that contain only one pigment. In order to prevent such pigment flocculation, a pigment dispersing agent must be added to the paint. The most suitable pigment dispersing agent will often differ for pigments with different structural formulas, meaning that in an intermediate colored paint containing a plurality of pigments with different structural formulas, a plurality of pigment dispersing agents are used. However, the most suitable pigment dispersing agent for one pigment may adversely affect the dispersibility of another pigment within the paint, thereby causing flocculation and a deterioration in the dispersion stability. Accordingly, in those cases where a plurality of pigment dispersing agents are combined, considerable care must be taken with the actual combination used.

Methods of generating an intermediate colored paint that involve the blending of pigments with similar structural formulas but a plurality of different hues also exist. Examples of pigments with similar structural formulas but a plurality of different hues include the benzimidazolone based compounds represented by a formula (2) (hereafter referred to as the "compound (2)") and a formula (3) (hereafter referred to as the "compound (3)") shown below (see W. Herbst and K. Hunger, "Industrial Organic Pigments, second completely revised edition" VCH Verlagsgesellschaft mbH, 1997, pp. 345 to 370).

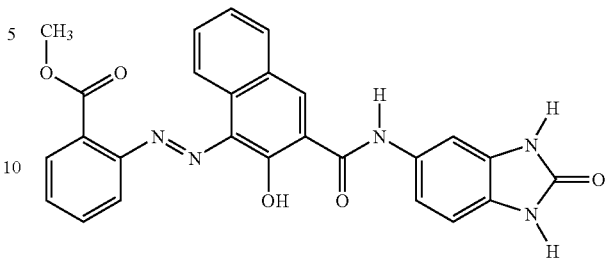

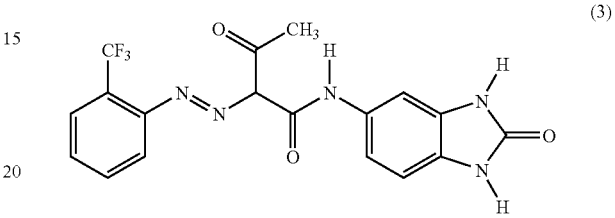

These benzimidazolone based compounds are known to form a red to brown colored pigment when the molecular structure includes a naphthalene ring (the compound (2) shown above is red), and a yellow to orange colored pigment when the molecular structure does nor contain a naphthalene ring (the compound (3) shown above is yellow).

However, even in a paint prepared by blending the structurally similar compounds (2) and (3), the pigments still tend to flocculate, making it difficult to achieve the desired hue.

DISCLOSURE OF INVENTION

An object of the present invention is to provide benzimidazolone compounds that provide a plurality of hues from a single structural formula, and are useful as pigments that offer superior dispersibility in binder resins, and to provide benzimidazolone compounds that are useful as pigments, and show minimal flocculation when two or more pigments of different hues are blended together to produced a desired hue.

As a result of intensive investigation aimed at achieving the above object, based on the concept that if a compound with a single structural formula displays a plurality of different hues, then generating an intermediate color by blending these different hues should enable suppression of pigment flocculation, the inventors of the present invention discovered that benzimidazolone compounds with introduced functional groups that enable the formation, through intramolecular hydrogen bonding, of three six-membered rings in a planar structure display a plurality of different hues, even with the same structural formula. In addition, they also discovered that these benzimidazolone compounds were able to generate a paint with superior dispersion stability and no varnish separation, without the addition of pigment dispersing agents, both in cases where a pigment of a single hue was used, and in cases where pigments with different hues were blended together.

In other words, the present invention provides a benzimidazolone compound represented by a general formula (1) shown below.

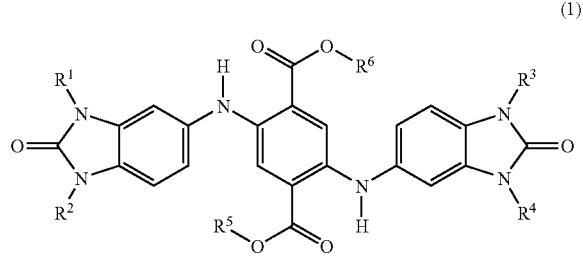

(1)

(wherein, $R^1$, $R^2$, $R^3$ and $R^4$ each represent, independently, a hydrogen atom, an alkyl group of 1 to 5 carbon atoms, or an alkoxy group of 1 to 5 carbon atoms, and $R^5$ and $R^6$ each represent, independently, an alkyl group of 1 to 5 carbon atoms.)

The benzimidazolone compounds represented by the general formula (1) display excellent dispersion stability even without the addition of a pigment dispersing agent, meaning they are ideal as colored pigments for printing inks, paints, colorants for various plastics, toner, inkjet inks, and color filters and the like. The compound in which the groups $R^1$, $R^2$, $R^3$ and $R^4$ in the above general formula (1) are all hydrogen atoms, and the groups $R^5$ and $R^6$ are both methyl groups, while representing a single structural formula, displays a variety of different hues including vivid red, yellow, reddish purple, and bluish red, depending on certain variations in the crystal structure, and is consequently particularly preferred. Because these pigments provide superior suppression of pigment flocculation they are extremely useful, regardless of whether a single pigment is used, or two or more pigments with different hues are blended together to generate an intermediate color.

BEST MODE FOR CARRYING OUT THE INVENTION

Synthetic Method 1

Figure 1:
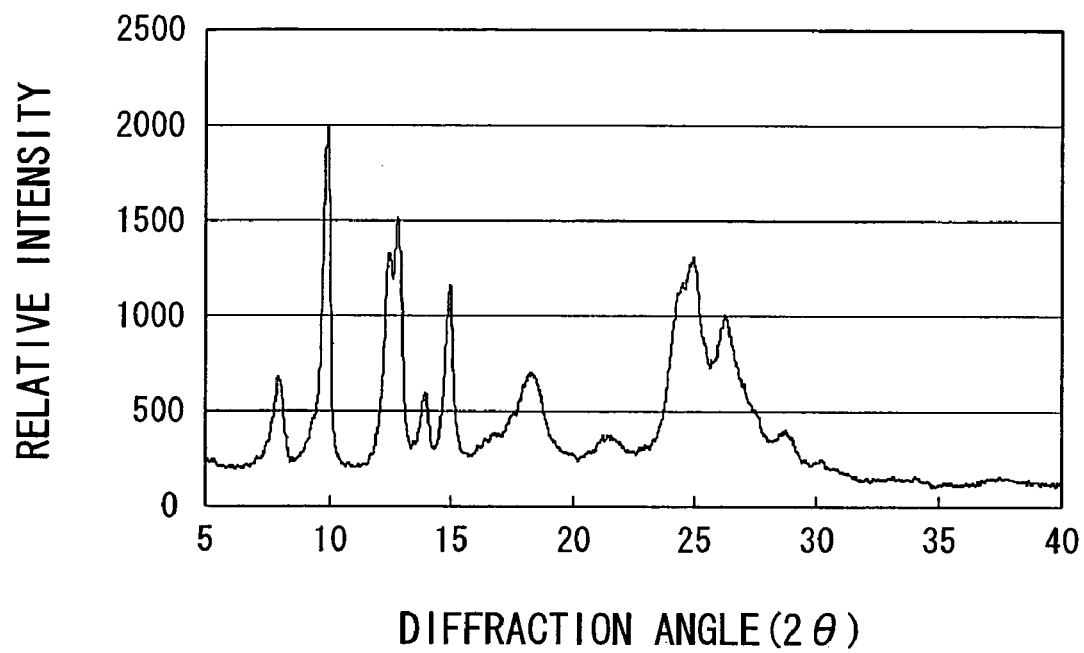
FIG. 1 is an X-ray diffraction plot of α-type crystal of a compound (1H) of the present invention obtained in an example 1.

A benzimidazolone compound of the general formula (1), in which $R^1$ and $R^4$ represent the same group, and $R^2$ and $R^3$ represent the same group, can be prepared by reacting 1 equivalent of a compound represented by a general formula (4) shown below (hereafter referred to as the "compound (4)"), 1 equivalent of a compound represented by a general formula (5) shown below (hereafter referred to as the "compound (5)"), and 1 equivalent of a compound represented by a general formula (6) shown below (hereafter referred to as the "compound (6)") in an aprotic polar solvent such as 1,3-dimethyl-2-imidazolidinone, dimethylsulfoxide, N,N-dimethylformamide, or N-methyl-2-pyrrolidone, in the presence of an acid such as sulfuric acid, hydrochloric acid, or phosphoric acid, for 8 to 14 hours at a temperature of 150 to 180° C., and then cooling the reaction mixture to room temperature, and filtering, washing, drying, and crushing the precipitated crystals using normal methods.

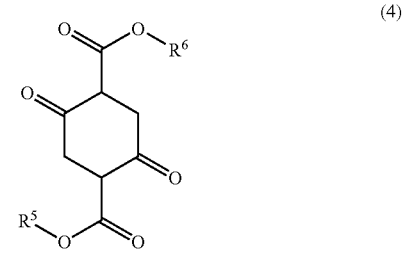

(4)

(wherein, $R^5$ and $R^6$ each represent, independently, an alkyl group of 1 to 5 carbon atoms.)

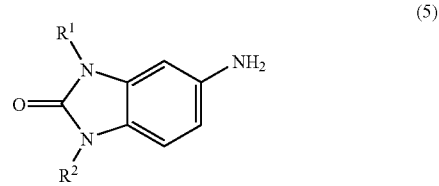

(5)

(wherein, $R^1$ and $R^2$ each represent, independently, a hydrogen atom, an alkyl group of 1 to 5 carbon atoms, or an alkoxy group of 1 to 5 carbon atoms.)

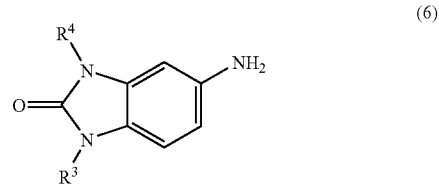

(6)

(wherein, $R^3$ and $R^4$ each represent, independently, a hydrogen atom, an alkyl group of 1 to 5 carbon atoms, or an alkoxy group of 1 to 5 carbon atoms.)

Synthetic Method 2

A benzimidazolone compound of the general formula (1), in which $R^1$ and $R^4$ represent different groups, or $R^2$ and $R^3$ represent different groups, can be prepared under the same reaction conditions as the synthetic method 1 described above, by first reacting 1 equivalent of the compound (4) and 1 equivalent of the compound (5), subsequently reacting the resulting reaction product with the compound (6), and then cooling the resulting product to room temperature, and filtering, washing, drying, and crushing the precipitated crystals using normal methods.

Of the compounds represented by the general formula (1), a compound of the general formula (1) represented by a formula (7) shown below (hereafter referred to as the "compound (7)"), in which $R^1$, $R^2$, $R^3$ and $R^4$ all represent hydrogen atoms, and $R^5$ and $R^6$ both represent methyl groups, enables the preparation of 4 different crystal types, namely α-type crystal, β-type crystal, γ-type crystal and δ-type crystal described below, all with the same structural formula, and is consequently preferred.

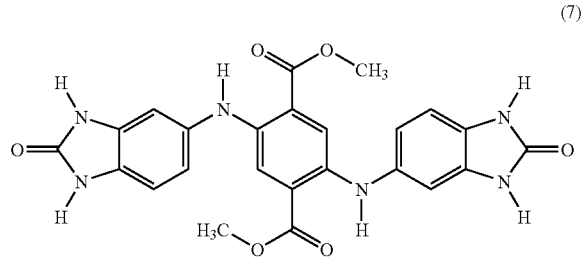

(7)

(α-Type Crystal)

(1) X-Ray Diffraction Peaks

Displays diffraction peaks for Cu—Kα characteristic X-rays at Bragg angles 2θ of 9.9±0.2°, 12.8±0.2°, 15.0±0.2°, and 25.0±0.2°.

(2) Hue

A vivid red color.

(3) Production Method

Can be produced using the synthetic method 1 described above.

(β-Type Crystal)

(1) X-Ray Diffraction Peaks

Displays diffraction peaks for Cu—Kα characteristic X-rays at Bragg angles 2θ of 14.3±0.2°, 16.6±0.2°, 24.2±0.2°, and 24.8±0.2°.

(2) Hue

A vivid yellow color.

(3) Production Method

Heating the above α-type crystal in N,N-dimethylformamide at a temperature of 60 to 120° C. causes the red crystals to gradually change color to yellow crystals. After heating for at least 6 hours, the β-type crystal can be obtained by cooling the mixture to room temperature, and filtering, washing, and drying the crystals using normal methods.

(γ-Type Crystal)

(1) X-Ray Diffraction Peaks

Displays diffraction peaks for Cu—Kα characteristic X-rays at Bragg angles 2θ of 9.9±0.2°, 14.3±0.2°, 16.3±0.2°, 24.5±0.2°, and 26.0±0.2°.

(2) Hue

A vivid reddish purple color.

(3) Production Method

The γ-type crystal can be obtained by grinding and mixing the above α-type crystal, together with a water-soluble inorganic salt such as sodium chloride or sodium sulfate as a grinding medium, and a liquid grinding auxiliary agent such as diethylene glycol, using a device that applies a mechanical shearing force to the mixture such as a ball mill, an atriter, a vibration mill, or a kneader, subsequently peptizing the ground mixture using a solvent that dissolves the grinding medium and the liquid grinding auxiliary agent but does not dissolve the crystals, and then filtering, washing, drying, and crushing the crystals using normal methods.

(δ-Type Crystal)

(1) X-Ray Diffraction Peaks

Displays diffraction peaks for Cu—Kα characteristic X-rays at Bragg angles 2θ of 12.8±0.2°, 15.8±0.2°, 25.0±0.2°, and 26.5±0.2°.

(2) Hue

A vivid bluish red color.

(3) Production Method

The δ-type crystal can be obtained by dissolving the above α-type crystal, β-type crystal, or γ-type crystal in concentrated sulfuric acid, pouring the solution into ice water to effect re-precipitation, thus precipitating bluish red crystals, and then filtering the bluish red colored slurry, and washing, drying, and crushing the crystals using normal methods.

The reason that the four crystal types described above have mutually different hues is not understood in great detail, although it is surmised that the following factors are significant.

The compound (7) comprises a single aromatic ring at the center of the structure. If the two amino groups and the carbonyl groups of the two carboxylate ester groups bonded to this aromatic ring form intramolecular hydrogen bonds, then a structure is formed in which three six-membered rings, including the central aromatic ring, are aligned in sequence (see formula (8) below). The plane formed by these three six-membered rings represents a chromophore, and is believed to be responsible for generating the hue of the red based crystals (the α-type crystal, γ-type crystal, and δ-type crystal).

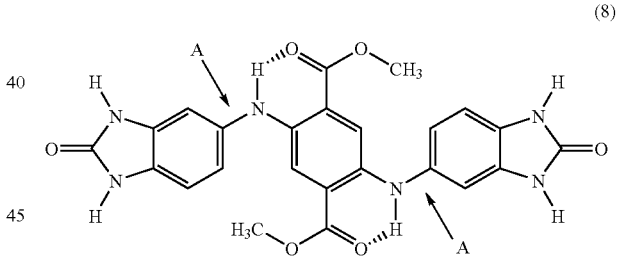

(8)

Furthermore, the reason that the hue differs between the α-type crystal, the γ-type crystal, and the δ-type crystal is thought to be due to the fact that the angle between the plane formed by the three six-membered rings, including the central aromatic ring, formed as a result of intramolecular hydrogen bonding, and the plane of the benzimidazolone groups, varies in the different crystal types as a result of rotation about the bonds indicated by the arrows "A" in the above formula (8).

On the other hand, it is believed that if the intramolecular hydrogen bonds formed between the two amino groups and the carbonyl groups of the two carboxylate ester groups are broken by heating within an organic solvent, then the portion of the molecule that forms the plane representing the chromophore in the center of the molecule is reduced to just the central aromatic ring, meaning its contribution as a chromophore diminishes, thus yielding crystals with a yellow hue (the β-type crystal).

EXAMPLES

As follows is a more detailed description of the present invention, based on a series of examples. Unless stated otherwise, the units "parts" and "%" in the examples refer to weight referenced values.

Example 1

43.6 parts of 5-aminobenzimidazolone, 30 parts of dimethylsuccinyl succinate, and 13.4 parts of concentrated sulfuric acid were added to 750 parts of 1,3-dimethyl-2-imidazolidinone, and the resulting mixture was heated for 14 hours at 180° C. Following cooling to room temperature, the precipitate was filtered, washed with 200 parts of 1,3-dimethyl-2-imidazolidinone and 600 parts of acetone to remove impurities, and then dried under reduced pressure for 8 hours at 110° C., thus yielding 17.7 parts (yield 28%) of vivid red colored α-type crystal. When these red α-type crystal were analyzed by infrared spectroscopy and field desorption mass spectrometry (FD-MS), the following results were obtained.

Infrared Spectroscopy

Infrared spectroscopic analysis using a Fourier transform infrared spectrophotometer FT/IR-550 manufactured by Jasco Corporation revealed absorption peaks due to the following stretching vibrations.

$3200$ $cm^{-1}$: N—H stretching vibration for the amide groups within the imidazolone rings
$1720$ $cm^{-1}$: C=O stretching vibration for the methyl esters.
$1695$ $cm^{-1}$: C=O stretching vibration within the imidazolone rings.
$1220$ $cm^{-1}$: C—O stretching vibration for the methyl esters.

Field Desorption Mass Spectrometry (FD-MS)

Field desorption mass spectrometric analysis using a (double focus type) gas chromatograph mass spectrometer GCMS 9100MK manufactured by Shimadzu Corporation detected a molecular ion peak at a molecular weight of 488.

The results of the above analyses identified the red α-type crystal obtained in the example 1 as crystals of the aforementioned compound (7).

In addition, a powder X-ray diffraction analysis using Cu—Kα X-ray radiation was also conducted on the red α-type crystal obtained in the example 1, using an X-ray diffraction apparatus RINT Ultima+ manufactured by Rigaku Corporation, and under the conditions listed below.

Power: 40 kV, 30 mA
Sampling angle: 0.020°
Divergence/scattering slit: (½)
Emission slit: 0.3 mm
Scan speed: 2°/minute The X-ray diffraction pattern obtained from the above powder X-ray diffraction analysis is shown in FIG. 1. The red α-type crystal of the compound (7) displayed diffraction peaks for Cu—Kα characteristic X-rays at Bragg angles 2θ of 9.9±0.2°, 12.8±0.2°, 15.0±0.2°, and 25.0±0.2°.

Example 2

2 parts of the red α-type crystal obtained in the example 1 were added to 10 parts of N,N-dimethylformamide, and the mixture was heated for 6 hours at 90° C. The resulting mixture was then cooled to room temperature, the slurry was filtered and washed with 50 parts of acetone, and the resulting precipitate was then dried under reduced pressure for 8 hours at 110° C., thus yielding 1.6 parts (yield 80%) of vivid yellow colored β-type crystal.

Figure 2:
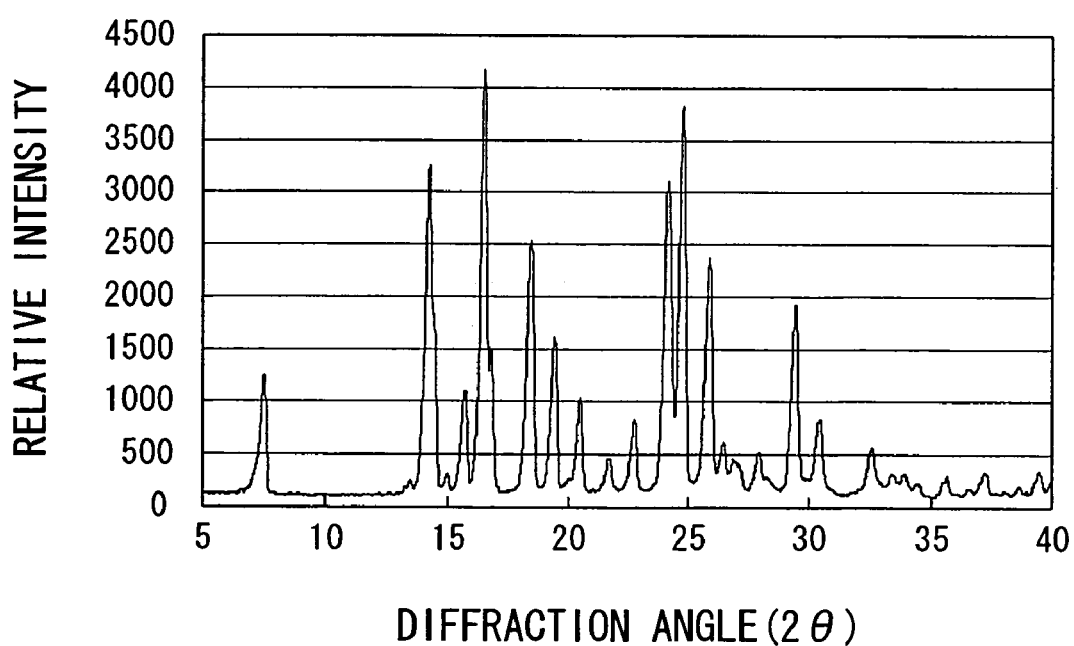
FIG. 2 is an X-ray diffraction plot of β-type crystal of a compound (1H) of the present invention obtained in an example 2.

These yellow β-type crystal were analyzed by powder X-ray diffraction using the same method as that described for the red α-type crystal obtained in the example 1. The resulting X-ray diffraction pattern is shown in FIG. 2. The crystals were shown to be different from the α-type crystal, and displayed diffraction peaks for Cu—Kα characteristic X-rays at Bragg angles 2θ of 14.3±0.2°, 16.6±0.2°, 24.2±0.2°, and 24.8±0.2°.

Example 3

15 parts of the red α-type crystal obtained in the example 1, 150 parts of table salt, and 37.5 parts of diethylene glycol were mixed together and ground in a kneader. The resulting mixture was then peptized in 1000 parts of water at 60° C. and subsequently filtered. A washing process, in which the thus obtained wet cake was peptized in 1000 parts of water at 60° C. and then filtered, was repeated 3 times. The washed wet cake was then dried under reduced pressure for 8 hours at 110° C., thus yielding 13.5 parts (yield 90%) of vivid reddish purple colored γ-type crystal.

Figure 3:
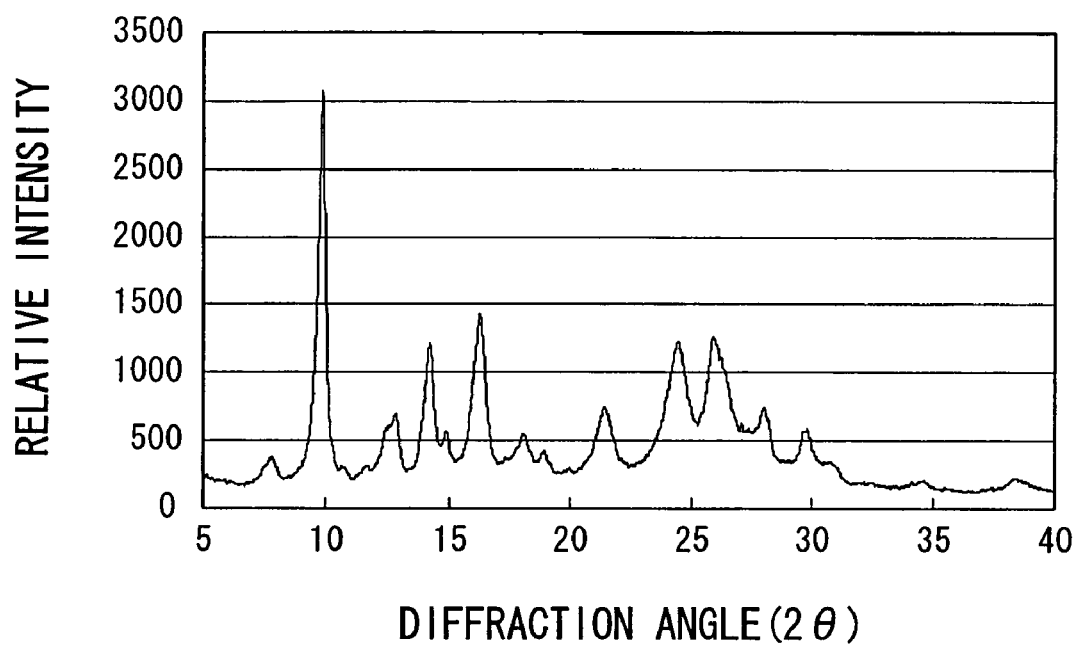
FIG. 3 is an X-ray diffraction plot of γ-type crystal of a compound (1H) of the present invention obtained in an example 3.

These reddish purple γ-type crystal were analyzed by powder X-ray diffraction using the same method as that described for the red α-type crystal obtained in the example 1. The resulting X-ray diffraction pattern is shown in FIG. 3. The crystals were shown to be different from both the α-type crystal and the β-type crystal, and displayed diffraction peaks for Cu—Kα characteristic X-rays at Bragg angles 2θ of 9.9±0.2°, 14.3±0.2°, 16.3±0.2°, 24.5±0.2°, and 26.0±0.2°.

Example 4

2 parts of the red α-type crystal obtained in the example 1 were dissolved in 10 parts of concentrated sulfuric acid (sulfuric acid concentration of at least 95%). The resulting sulfuric acid solution was then poured into 100 parts of water, thus precipitating red crystals and generating a slurry. The slurry was filtered, and then washed repeatedly with water until the filtrate became neutral. The washed wet cake was then dried under reduced pressure for 8 hours at 110° C., yielding 1.8 parts (yield 90%) of bluish red colored δ-type crystal.

Figure 4:
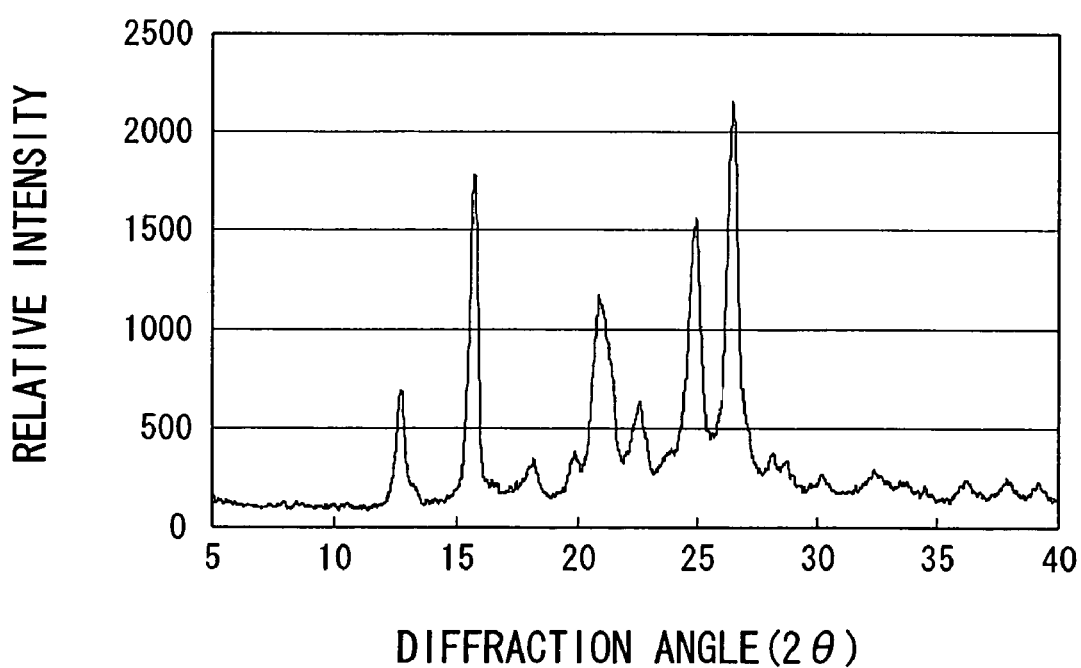
FIG. 4 is an X-ray diffraction plot of δ-type crystal of a compound (1H) of the present invention obtained in an example 4.

These bluish red δ-type crystal were analyzed by powder X-ray diffraction using the same method as that described for the red α-type crystal obtained in the example 1. The resulting X-ray diffraction pattern is shown in FIG. 4. The crystals were shown to be different from the α-type, β-type, and γ-type crystal, and displayed diffraction peaks for Cu—Kα characteristic X-rays at Bragg angles 2θ of 12.8±0.2°, 15.8±0.2°, 25.0±0.2°, and 26.5±0.2°.

The hues and Cu—Kα characteristic X-ray peaks for each of the four crystal types obtained in the above examples 1 to 4 are summarized below in Table 1.

TABLE 1

| | Crystal type | | | |
|---|---|---|---|---|
| | α-type | β-type | γ-type | δ-type |
| Hue | Red | Yellow | Reddish purple | Bluish red |
| Cu-Kα characteristic X-ray peaks (±0.2°) | 9.9° | 14.3° | 9.9° | 12.8° |
| | 12.8° | 16.6° | 14.3° | 15.8° |
| | 15.0° | 24.2° | 16.3° | 25.0° |
| | 25.0° | 24.8° | 24.5° | 26.5° |
| | | | 26.0° | |

Example 5

66 parts of a mixed resin comprising 70% of a baking paint alkyd resin (product name: Beckosol J-524-IM-60, manufactured by Dainippon Ink and Chemicals, Incorporated) and 30% of a melamine resin (product name: Super Beckamine G-821-60, manufactured by Dainippon Ink and Chemicals, Incorporated) was dissolved in 12 parts of a mixed solvent of xylene:n-butanol=7:3, thus yielding a binder resin solution.

2 parts of the α-type crystal obtained in the example 1 were added to 78 parts of this binder resin solution, and the mixture was shaken and dispersed for 2 hours in a paint conditioner, thus yielding a paint (1).

Example 6

With the exception of replacing the α-type crystal used in the example 5 with the β-type crystal obtained in the example 2, a paint (2) was prepared in the same manner as the example 5.

Example 7

5 parts of the paint (1) obtained in the example 5 and 5 parts of the paint (2) obtained in the example 6 were mixed together, forming 10 parts of a mixed paint (1).

Comparative Example 1

With the exception of replacing the α-type crystal used in the example 5 with a red pigment (product name: Irgazin DPP Red BO (C.I. Pigment Red 254), manufactured by Ciba Specialty Chemicals Corporation, hereafter abbreviated as DPP-BO), a paint (3) was prepared in the same manner as the example 5.

Comparative Example 2

With the exception of replacing the α-type crystal used in the example 5 with a red pigment (product name: Novoperm Red HFT (C.I. Pigment Red 175), manufactured by Clariant Japan K.K., equivalent to the aforementioned compound (2), hereafter abbreviated as HFT), a paint (4) was prepared in the same manner as the example 5.

Comparative Example 3

With the exception of replacing the α-type crystal used in the example 5 with a yellow pigment (product name: Symuler Fast Yellow 4192 (C.I. Pigment Yellow 154), manufactured by Dainippon Ink and Chemicals, Incorporated, equivalent to the aforementioned compound (3), hereafter abbreviated as 4192), a paint (5) was prepared in the same manner as the example 5.

Comparative Example 4

5 parts of the paint (3) obtained in the comparative example 1 and 5 parts of the paint (5) obtained in the comparative example 3 were mixed together, forming 10 parts of a mixed paint (2).

Comparative Example 5

5 parts of the paint (4) obtained in the comparative example 2 and 5 parts of the paint (5) obtained in the comparative example 3 were mixed together, forming 10 parts of a mixed paint (3).

Evaluation of Paint Flocculation

For each of the paints prepared in the above examples 5 to 7 and the comparative examples 1 to 5, the volumetric average particle size of the pigment within the paint immediately following preparation was measured using a Microtrac Particle Size Analyzer UPA150, manufactured by Nikkiso Co., Ltd. Furthermore, the volumetric average particle size of the pigment within each paint following standing for 1 day at room temperature was also measured in the same manner. In addition, the difference in the volumetric average particle size (Δ average particle size) for each paint was also calculated by subtracting the value of the volumetric average particle size immediately following preparation from the value of the volumetric average particle size following standing for 1 day. This value for Δ average particle size was used to evaluate the level of flocculation, based on the following evaluation standards.

A: Δ average particle size of less than 0.20 μm, B: Δ average particle size of at least 0.20 μm Evaluation of Paint Varnish Separation A sample of each of the paints prepared in the above examples 5 to 7 and the comparative examples 1 to 5 was placed in a transparent glass sample vial, and allowed to stand for 2 weeks at room temperature. The samples were then inspected visually for evidence of varnish separation (separation of the pigment and the resin solution, leading to the generation of a transparent resin solution layer at the top of the paint sample). The results obtained were used to evaluate the varnish separation, based on the following evaluation standards.

A: no varnish separation observed, B: varnish separation observed

The results of the evaluations of each of the paints prepared in the above examples 5 to 7 and the comparative examples 1 to 5 are summarized below in Table 2.

TABLE 2

|  | Example 5 | Example 6 | Example 7 | Comparative Example 1 | Comparative Example 2 | Comparative Example 3 | Comparative Example 4 | Comparative Example 5 |
|---|---|---|---|---|---|---|---|---|
| Paint | Paint (1) | Paint (2) | Mixed paint (1) | Paint (3) | Paint (4) | Paint (5) | Mixed paint (2) | Mixed paint (3) |
| Pigment crystal | α type crystal | β type crystal | α and β type crystals | DPP-BO | HFT | 4192 | DPP-BO 4192 | HFT 4192 |
| Average particle size of pigment immediately after preparation (μm) | 0.97 | 1.49 | 1.26 | 1.14 | 0.87 | 1.55 | 1.44 | 1.89 |

TABLE 2-continued

| | Example 5 | Example 6 | Example 7 | Comparative Example 1 | Comparative Example 2 | Comparative Example 3 | Comparative Example 4 | Comparative Example 5 |
|---|---|---|---|---|---|---|---|---|
| Average particle size of pigment after standing for 1 day (μm) | 0.95 | 1.34 | 1.25 | 1.37 | 1.20 | 1.81 | 1.65 | 2.45 |
| Δ average particle size (μm) | −0.02 | −0.15 | −0.01 | 0.23 | 0.33 | 0.26 | 0.21 | 0.56 |
| Paint flocculation | A | A | A | B | B | B | B | B |
| Paint varnish separation | A | A | A | B | B | B | B | B |

From the results shown in Table 2, the following observations were made.

From the results for the examples 5 and 6 it is evident that when the α-type crystal or the β-type crystal of a benzimidazolone compound of the present invention were used individually within a paint, neither pigment flocculation nor varnish separation occurred.

From the results for the example 7 it is evident that when a paint containing the α-type crystal of a benzimidazolone compound of the present invention was mixed with a paint containing the β-type crystal of the benzimidazolone compound, neither pigment flocculation nor varnish separation occurred.

From the results for the comparative examples 1, 2, and 3 it is evident that when a conventional pigment such as DPP-BO, HFT, or 4192 was used individually within a paint, both pigment flocculation and varnish separation occurred.

From the results for the comparative example 4 it is evident that when a paint (3) containing the conventional pigment DPP-BO was mixed with a paint (5) containing the pigment 4192, both pigment flocculation and varnish separation occurred.

The comparative example 5 represents an example in which a paint (4) containing the conventional pigment HFT was mixed with a paint (5) containing the pigment 4192, which has a similar structural formula to that of HFT, but it is clear that pigment flocculation and varnish separation still occurred in this example. Furthermore, the average particle size of the pigment within the paint (4) containing the pigment HFT was 0.87 μm, and the average particle size of the pigment within the paint (5) containing the pigment 4192 was 1.55 μm, and as a result, it was expected that the average particle size for the pigment within the mixed paint (3), comprising a mixture of equal quantities of these two paints, would be the average of these two average particle sizes, namely 1.21 μm. However, the measured value for the average particle size immediately following mixing of the two paints was 1.89 μm, indicating that pigment flocculation had occurred immediately upon mixing of the two paints.

INDUSTRIAL APPLICABILITY

Benzimidazolone compounds of the present invention represented by a general formula (1) display excellent dispersion stability even without the addition of a pigment dispersing agent, meaning they are ideal as colored pigments for printing inks, paints, colorants for various plastics, toner, inkjet inks, and color filters and the like. The compound of the general formula (1) in which the groups $R^1$, $R^2$, $R^3$ and $R^4$ are all hydrogen atoms, and the groups $R^5$ and $R^6$ are both methyl groups, while representing a single structural formula, displays a variety of different hues including vivid red, yellow, reddish purple, and bluish red, depending on certain variations in the crystal structure, and is consequently particularly preferred. Because these pigments provide superior suppression of pigment flocculation they are extremely useful, regardless of whether a single pigment is used, or two or more pigments with different hues are blended together to generate an intermediate color.

The invention claimed is:

1. A benzimidazolone compound represented by a general formula (1) shown below:

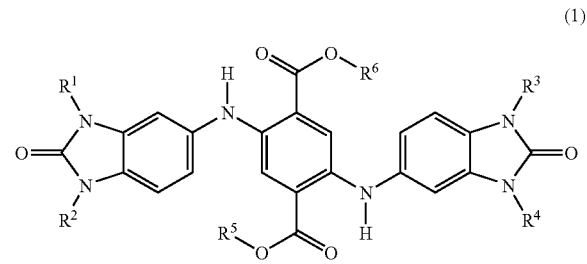

(1)

(wherein, $R^1$, $R^2$, $R^3$ and $R^4$ each represent, independently, a hydrogen atom, an alkyl group of 1 to 5 carbon atoms, or an alkoxy group of 1 to 5 carbon atoms, and $R^5$ and $R^6$ each represent, independently, an alkyl group of 1 to 5 carbon atoms).

2. A benzimidazolone compound according to claim 1, wherein in said general formula (1), $R^1$, $R^2$, $R^3$ and $R^4$ all represent hydrogen atoms, and $R^5$ and $R^6$ both represent methyl groups.

3. A benzimidazolone compound according to claim 2, which displays diffraction peaks for Cu—Kα characteristic X-rays at Bragg angles 2θ of 9.9±0.2°, 12.8±0.2°, 15.0±0.2°, and 25.0±0.2°.

4. A benzimidazolone compound according to claim 2, which displays diffraction peaks for Cu—Kα characteristic X-rays at Bragg angles 2θ of 14.3±0.2°, 16.6±0.2°, 24.2±0.2°, and 24.8±0.2°.

5. A benzimidazolone compound according to claim 2, which displays diffraction peaks for Cu—Kα characteristic X-rays at Bragg angles 2θ of 9.9±0.2°, 14.3±0.2°, 16.3±0.2°, 24.5±0.2°, and 26.0±0.2°.

6. A benzimidazolone compound according to claim 2, which displays diffraction peaks for Cu—Kα characteristic X-rays at Bragg angles 2θ of 12.8±0.2°, 15.8±0.2°, 25.0±0.2°, and 26.5±0.2°.

* * * * *